(12) United States Patent
Nonaka

(10) Patent No.: US 7,168,423 B2
(45) Date of Patent: Jan. 30, 2007

(54) GAS SENSOR UNITS FOR ENGINES

(75) Inventor: Takumi Nonaka, Iwate-ken (JP)

(73) Assignee: Zama Japan Co., Ltd., Iwate-ken (JP)

( * ) Notice: Subject to any disclaimer, the term of this patent is extended or adjusted under 35 U.S.C. 154(b) by 0 days.

(21) Appl. No.: 11/191,085

(22) Filed: Jul. 28, 2005

(65) Prior Publication Data

US 2006/0081227 A1    Apr. 20, 2006

(30) Foreign Application Priority Data

Oct. 20, 2004    (JP) .............................. 2004-305760

(51) Int. Cl.
*F02D 41/14*    (2006.01)
(52) U.S. Cl. ...................... 123/703; 123/672; 73/31.05
(58) Field of Classification Search ................ 123/703, 123/672
See application file for complete search history.

(56) References Cited

U.S. PATENT DOCUMENTS

| | | | | |
|---|---|---|---|---|
| 4,339,320 A | * | 7/1982 | Friese et al. ................. 204/408 |
| 4,520,764 A | | 6/1985 | Ozawa | |
| 4,674,459 A | | 6/1987 | Blocher | |
| 4,796,425 A | | 1/1989 | Nagai | |
| 4,861,238 A | * | 8/1989 | Kamiyama et al. ......... 417/363 |
| 5,682,870 A | | 11/1997 | Motoyama | |
| 5,709,193 A | | 1/1998 | Svensson | |
| 5,899,443 A | * | 5/1999 | Su ......................... 267/140.14 |
| 6,068,530 A | * | 5/2000 | Ozawa ...................... 440/88 A |
| 6,135,100 A | * | 10/2000 | Katoh ........................ 123/679 |
| 6,202,472 B1 | * | 3/2001 | Wezurek et al. ........... 73/31.05 |
| 6,318,329 B1 | * | 11/2001 | Sato ......................... 123/192.1 |
| 6,326,704 B1 | * | 12/2001 | Breed et al. ................. 307/9.1 |
| 6,431,149 B1 | * | 8/2002 | Schwegler et al. ......... 123/467 |
| 6,907,870 B2 | | 6/2005 | zur Loye | |
| 7,004,146 B1 | * | 2/2006 | Kato ........................... 123/467 |
| 2005/0235974 A1 | | 10/2005 | Nonaka | |

FOREIGN PATENT DOCUMENTS

| JP | 1999281612 A | 10/1999 |
|---|---|---|
| JP | 2002071625 A | 12/2002 |

* cited by examiner

*Primary Examiner*—Erick Solis
(74) *Attorney, Agent, or Firm*—Baker Botts L.L.P.

(57) ABSTRACT

In a multipurpose engine with a reduced or limited displacement adapted for use in a portable work machine or the like, the engine includes a detecting element of a gas sensor for controlling an air-fuel ratio. Damage or degradation of the detecting element due to vibration from the engine is reduced or eliminated. To achieve this, a supporting device having a vibration-damping-function is provided for supporting the gas sensor or the gas sensor unit containing the gas sensor. The supporting device permits the gas sensor or the gas sensor unit to move by an amount equal to or less than a predetermined extent of movement of the engine, so that the transmission of vibration from the engine directly to the gas sensor is reduced or eliminated.

20 Claims, 5 Drawing Sheets

GAS SENSOR UNITS FOR ENGINES

BACKGROUND OF THE INVENTION

1. Field of the Invention

The present invention relates to gas sensor units adapted for use in apparatus for controlling an air-to-fuel ratio (hereinafter the "air-fuel ratio") of engines.

2. Description of Related Art

It is known that, in order to maintain an engine in satisfactory operating condition while reducing hazardous ingredients contained in the exhaust gas from the engine, eg., automobile engines, to comply with the exhaust gas regulations, a gas sensor, such as an $O_2$ sensor, is used for controlling fuel flow to achieve the stoichiometric, air-fuel ratio. Moreover, a three-way catalyst may be used to make the exhaust gas harmless or less harmful.

Nevertheless, if the above-mentioned methods are adopted for controlling the air-fuel ratio by regulating the fuel flow in a carburetor, a control unit with a significant volume may be required, in addition to the $O_2$ sensor and the three-way catalyst. As a result, the engine may increase significantly in size, complexity, weight, and cost. Therefore, it will be difficult to adopt such a system, particularly for a light, which require reduced or limited size and weight.

Consequently, an alternative air-fuel ratio control system may be provided in which the density of a particular hazardous ingredient is detected by using as an exhaust gas sensor. A gas sensor may be used, which is less expensive than the $O_2$ sensor, e.g., a gas sensor for detecting a combustible gas, such as carbon monoxide (hereinafter "CO"), hydrogen, hydrocarbons, or atmospheric gas. Thus, control of the air-fuel ratio may be accomplished by a control unit of relatively low volume, but which is capable of achieving the exhaust gas regulations at reduced cost and without using a three-way catalyst.

Nevertheless, such gas sensors for detecting combustible gas may be susceptible to damage or degradation due to vibration because such sensors have a finely constructed sensing element, such as a platinum coil formed by a fine wire with a diameter of about 10 μm. If such a sensor is positioned adjacent to the vibration source of the engine, the sensor may be damaged or degraded because vibration from the engine may be transmitted directly to the sensing element.

As a technique for protecting the exhaust gas sensor from damage or degradation due to vibration, a system is described in Unexamined Japanese Patent Publication No. 11(1999)-281612, in which a gas sensor has a casing to house therein a sensing element. The outside of the casing is covered by a combined filter-and-shock absorbing part. including a PTFE, hollow fiber structure for absorbing shocks from the outside. Another system is described in Unexamined Japanese Patent Publication No. 2002-71625, in which a frame element is provided between the sensing element of an $O_2$ sensor and a protruding part of a protective insulator so as to absorb shocks and vibration.

These techniques may be effective for preventing or reducing damage to or degradation of a sensing element by the use of a shock absorbing material, which stops shocks and vibration from transmitting directly to the exhaust gas sensor. These techniques, however, appear to be based upon the assumption that the vibrations are relatively weak due to their occurrence at a position to some extent apart from the engine forming the vibration source, or that shocks are transmitted from the outside, rather than upon the assumption that an exhaust gas sensor is disposed at a position adjacent to the engine, such as in a portable work machine, e.g., a chain saw, or an outboard machine. Therefore, these techniques may not protect against vibration or avoid or reduce damage or degradation by sufficiently absorbing vibration, which might transmit directly to the fragile sensing element.

SUMMARY OF THE INVENTION

An object of the present invention is to solve the above-mentioned problem, and, in particular, to protect a gas sensor used for controlling an air-fuel ratio of an engine in a machine, such as a portable work machine or an outboard machine or the like, against damage to or degradation of the sensing element due to vibration from the engine, such as when the gas sensor is disposed adjacent to the engine.

Therefore, in accordance with the present invention, in a gas sensor unit, a gas sensor for the detection of combustible gas is disposed in a sensor chamber of the unit and detects the density of a particular combustible gas ingredient in the exhaust gas exhausted from a cylinder of an engine. The gas sensor outputs a detection signal to a control unit. At least one of the above-mentioned gas sensor unit and the combustible gas sensor mounted in the gas sensor unit is supported so as to be movable by an amount equal to or less than a predetermined extent of movement of the engine by means for damping vibration. Thus, vibration from the engine is reduced or prevented from transmitting directly to the gas sensor unit.

In particular, when the gas sensor unit containing the gas sensor is mounted on the engine, either the gas sensor unit is mounted onto the engine so as to be movably supported by means for damping vibration, or the gas sensor unit is attached directly to the engine in which case the gas sensor is movably supported within a sensor chamber by means for damping vibration. In either configuration, vibration from the engine is not transmitted directly to the gas sensor thereby avoiding damage to or degradation of the sensing element while protecting the gas sensor from trouble due to the vibration.

Further, in embodying the freely movable mounting of the gas sensor unit onto the engine, if the means for damping vibration is provided with an elastic supporting member for supporting the gas sensor unit separated from the engine and an exhaust gas inlet pipe branching and extending from the exhaust pipe of the engine, which is connected to the gas sensor unit for conducting the exhaust gas to the sensor chamber, vibration damping may be achieved with a less complicated configuration. In addition, if a resin band formed in a ring-shape is used as the elastic supporting member for hanging the gas sensor unit from the engine, an elastic deformation of the ring-shape may absorb vibration sufficiently even if the gas sensor unit is disposed adjacent to the vibration source.

On the other hand, in embodying the movable support of the gas sensor within the sensor chamber of the gas sensor unit, which unit is fixedly attached to the engine, if the means for damping vibration is provided with an elastic supporting member for supporting the gas sensor separate from the inner wall of the sensor chamber, vibration damping may be achieved with a less complicated and more compact configuration. In this case, if an elastic member comprised of a vibration damping spring is used as the elastic supporting member, the vibration may be absorbed sufficiently. Further, if the elastic member comprising the vibration damping spring is arranged in a manner, such that at least the top side and the bottom side of the gas sensor are supported from the inner wall of the sensor chamber in at least two directions, not only the gas sensor may achieve sufficient mobility owing to its ability to move in all directions, but also the elastic member may reduce or prevent excessive movement or convergence of the movement.

In addition, when the above-mentioned gas sensor unit is fixed to the engine, if the gas sensor unit is attached fixedly to a carburetor and integrally formed with the engine, the invention is applicable to an existing engine. If an exhaust gas return path capable of directly returning at least a portion of the exhaust gas introduced in the sensor chamber to the carburetor, the exhaust gas may be purified without requiring new piping members. Moreover, even if a CO sensor having a platinum coil as a sensing element is used as the above-mentioned gas sensor, because damage to or degradation of the gas sensor may be prevented with the vibration damping function provided by the invention described above. Consequently, the significant usefulness of the sensor may be ensured.

According to the present invention in which a gas sensor or a gas sensor unit is disposed to move by a predetermined amount of movement with respect to the engine, even if the gas sensor unit is positioned adjacent to the engine, vibration transmitted to the sensing element may be absorbed or dampened sufficiently, and damage to or degradation of the gas sensor unit may be reduced or prevented.

Further objects, Features, and advantages of the present invention will be understood from the following detailed description of preferred embodiments of the present invention with reference to the accompanying Figures.

BRIEF DESCRIPTION OF THE DRAWINGS

Embodiments of the invention now are described with reference to the accompanying figures, which are given by way of example only and are not intended to limit the present invention.

DESCRIPTION OF PREFERRED EMBODIMENTS

A description of an embodiment of the present invention is provided herein below, with reference to the accompanying drawings.

Figure 1:
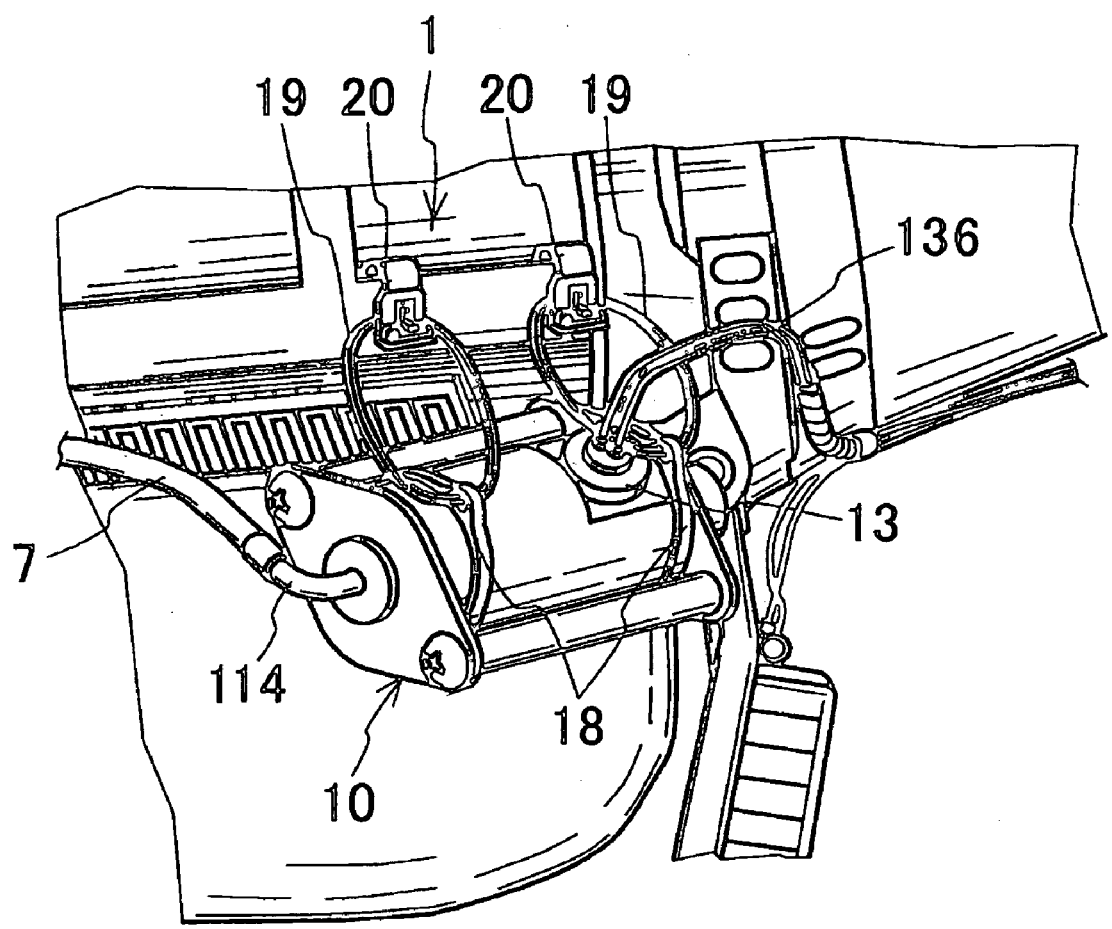
FIG. 1 is a perspective view of the gas sensor unit according to an embodiment of the present invention.

In the present invention, an engine is provided with a gas sensor unit mounted thereon, and the engine is configured to be relatively small in its size as a whole. Such an engine is mounted on a machine, for example, a portable work machine, an outboard machine, a passenger-carrying farming machine, motor cycle, or the like, in which the gas sensor unit is positioned adjacent to the body of the engine forming a source of vibration. Nevertheless, in the embodiment described herein below, the description is provided for a case in which an engine 1 is mounted on a portable work machine as illustrated in FIG. 1.

Engine 1 is configured to include a gas sensor unit 10 hanging from its side, and gas sensor unit 10 is a metal unit with a substantially cylindrical shape, to which an exhaust inlet pipe 7 branching from an exhaust pipe (not shown) of engine 1 is connected. Wirings also are provided for connecting a gas sensor 13 to a power supply and a control unit.

In addition, gas sensor unit 10 is supported so as to be suspended on the side of engine 1 by means of supporting devices 19, which are comprised of ring-like hanging bands made of elastic material, such as rubber or the like. and are arranged to pass through insertion openings 180, of ring-shape fixing belts 18. Ring-shaped fixing belts 18 are mounted to be fitted on respective ends of the unit and also to pass at the opposite sides thereof through metallic hanging fittings 20. Metallic hanging fittings 20 are fixedly hooked to portions of an external frame of engine 1.

Gas sensor 13 is constructed to have a sensing element that may be damaged or degraded due to vibration from engine 1. Gas sensor 13 may comprise one of various measuring systems including a contact burning-type system which measures a change in temperature of a heated wire during contact burning of the gas; a Carvarny buttery-type system, which measures an electrolysis current due to electrolysis with a gas; and a semi-conductor-type system, which measures a change in electric conductivity due to gas adsorption on the surface of a metal oxide, semi-conductor; and the like. In the present embodiment, a description is provided for gas sensor 13 in which a contact burning-type system of CO sensor is employed. In such a gas sensor, the sensing element is a platinum coil which is fragile and may be damaged or degraded when subjected to vibration. This sensor is relatively inexpensive and may be adapted for use as a measure of combustible gas in the exhaust gas to control the air-fuel ratio. Preferably, if CO gas forms a combustible gas and occupies a maximum of at least about 10% in the exhaust gas, this amount may be reduced to a level within a specified range meeting the exhaust gas standards or regulations.

The air-fuel ratio control apparatus provided with the gas sensor unit 10 according to the present embodiment of the invention controls an air-fuel ratio in such a way that the density or concentration of a particular hazardous ingredient in the exhaust gas generated by the operation of an engine, eg., the density of CO, is detected by gas sensor 13. A signal representing the detected density of CO is input to a control unit (not shown) and a determination is made whether or not the detected density of CO exceeds the exhaust gas standard or regulation value. If the detected density of CO exceeds the exhaust gas standard or regulation value, the fuel passage is closed during a predetermined period of time to temporarily cut off the fuel supply to thereby control the air-fuel ratio.

Figure 2:
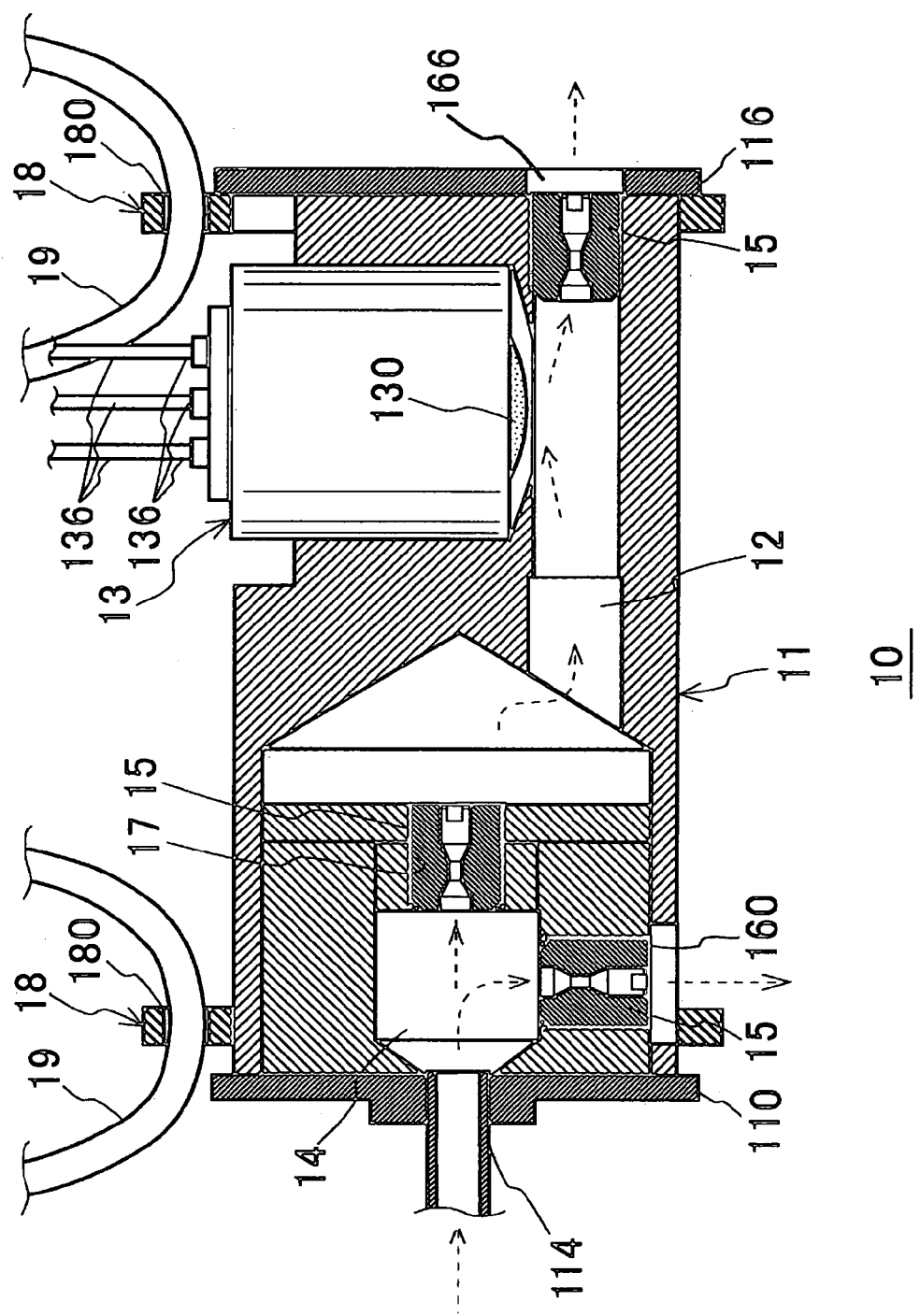
FIG. 2 is a vertical, cross-sectional view of the gas sensor unit of FIG. 1.

Subsequently, gas sensor unit 10 is described in detail, with reference to the vertical cross-sectional view of FIG. 2. Gas sensor unit 10, whose casing 11 is formed in a laterally extending and substantially cylindrical shape, is closed at both extreme ends thereof by cover parts 110, 112. Cover parts 110, 112 are fixed by screws or the like to casing 11. Gas sensor 10 is provided with a primary chamber 14 for initially receiving the exhaust gas therein, and a sensor chamber 12, disposed opposite to primary chamber 14, as a secondary chamber. Thus, gas sensor 13 is disposed within sensor chamber 12, so that a sensing portion 130, housing therein a sensing element, is exposed to exhaust gas within sensor chamber 12.

Primary chamber 14 is formed with a laterally extending and substantially cylindrical shape, in which a connecting pipe 114 connected to exhaust inlet pipe 7 is opened at its end on the side wall, such that primary chamber 14 is fluidly communicated with the exhaust pipe side of engine 1. Further, an exhaust vent 160 communicating with the atmosphere is opened on the bottom wall of primary chamber 14, and a cartridge-type of orifice (throttle) 15 is inserted fixedly therein to limit the exhaust gas flow to a predetermined value.

Sensor chamber 12 is composed of a larger diameter portion located on the side of primary chamber 14, and a smaller diameter portion in a laterally cylindrical shape which provides fluid communication between the larger diameter portion and exhaust vent 162 and is connected to primary chamber 14 through a communication vent 17. The smaller diameter portion of sensor chamber 12 has an inner surface, of which the central part permits sensing portion 130 of gas sensor 13 to be exposed from the upper side of the above-mentioned central part toward the inside the smaller diameter portion.

In addition, the communication vent 17 for fluidly connecting primary chamber 14 and sensor chamber 12 is provided with orifice 15 to limit the exhaust gas inflow to a predetermined value, so that the exhaust gas inflow from primary chamber 14 to sensor chamber 12 may be set to a predetermined value. If exhaust gas inflow is limited to an extent of one of several tenths to one of several hundredths of the inflow inlet into primary chamber 14, exhaust gas inflow is sufficient as a flow volume for measuring the combustible gas in the exhaust gas. On the other hand, exhaust vent 162 also is provided with orifice 15 so as to maintain the inside of sensor chamber 12 to be a little more highly pressurized than the atmosphere side. Although orifices 15 are arranged at three different positions, each orifice 15 is substantially identical having the same diameter in the present embodiment. Nevertheless, orifices 15 may be changed to have a different diameter, respectively, according to their purpose.

Means for damping vibration may comprise metallic hanging fittings 20 to hang or suspend gas sensor unit 10 to the side of engine 1, supporting device 19 comprising the hanging band, and fixing belt 18. Supporting device 19, which comprises the hanging band formed in a ring shape with high polymer resin, such as weather-proof nylon and the like, displays elasticity in substantially all directions. Supporting device 19 forms an indispensable element that supports (e.g., suspends or hangs) gas sensor unit 10 while absorbing most of the vibration transmitted from engine 1. Supporting device 19 comprising the hanging band also may be made of a commercially-available, bonding band by forming such a band into a ring shape of an appropriate size. Further, exhaust inlet pipe 7 may be made of soft and appropriately elastic resin. Therefore, exhaust inlet pipe 7 not only absorbs the vibration from engine 1, but also supports gas sensor unit 10 at the designated position aside and separated away from engine 1.

Gas sensor unit 10 of the present embodiment is configured as described above, and supporting devices 19 may sufficiently absorb the vibration and effectively prevent breakage of a wire of the platinum coil in sensing portion 130. Supporting devices 19 comprising the hanging band display elasticity in various directions even if gas sensor unit 10A is disposed adjacent to engine 1 that forms a vibration source.

Figure 3A:
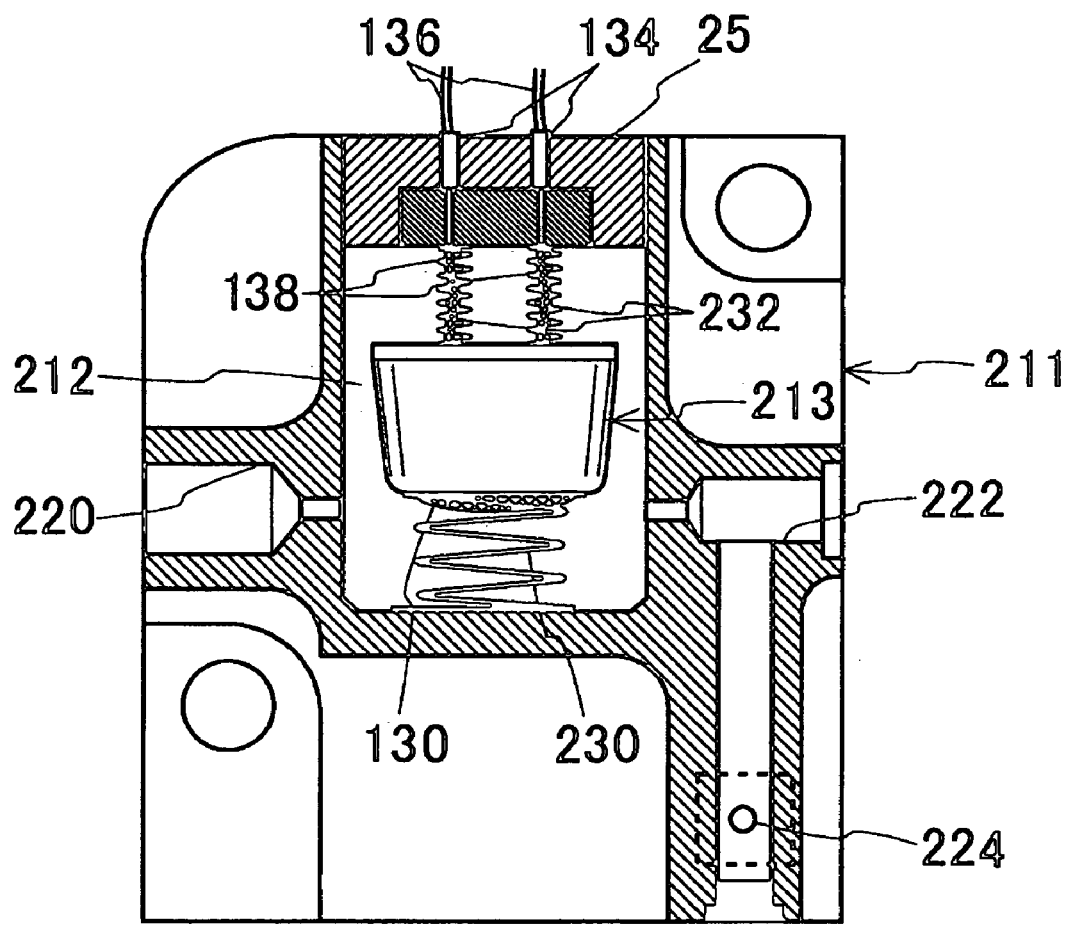
FIG. 3A is a vertical, cross-sectional view of a sensor unit according to another embodiment of the present invention.
Figure 3B:
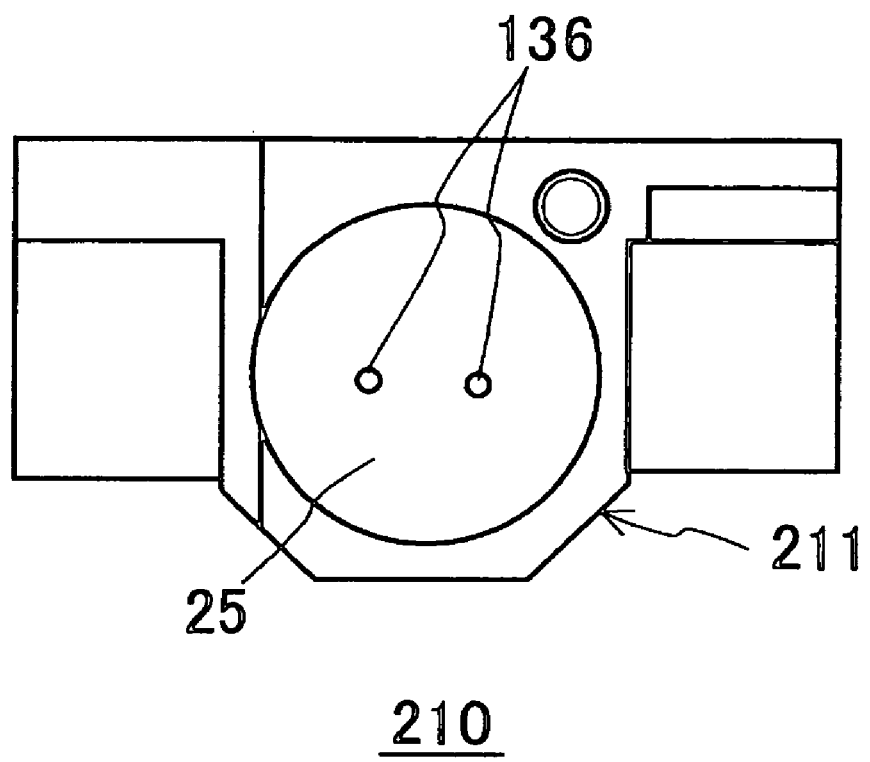
FIG. 3B is a top view of the gas sensor unit as depicted in FIG. 3A.
Figure 3C:
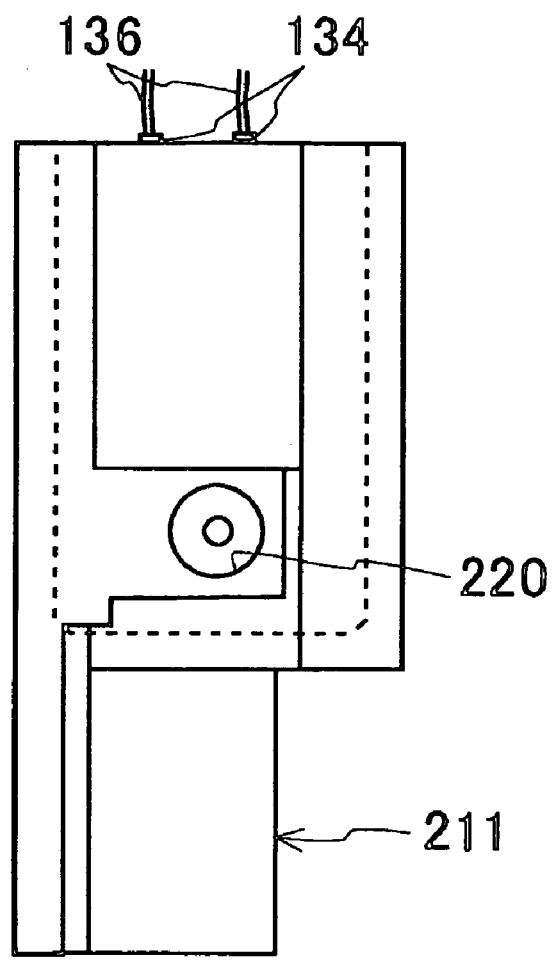
FIG. 3C is a side view of the gas sensor unit as depicted in FIG. 3A.

A description of another embodiment of the present invention is now provided. FIGS. 3A, 3B, and 3C depict, respectively, a vertical cross-sectional view, a top view, and a left side view of a gas sensor unit 210 in another embodiment, and gas sensor unit 210 is fixed to the side wall of a carburetor provided for engine 1. A gas sensor 213 is supported inside a sensor chamber 212 to be freely movable within a predetermined limit with respect to engine 1, by elastic supporting parts 230, and 232. Elastic supporting parts 230 and 232 comprise three supporting springs as the means for damping vibration.

As depicted in FIG. 3A, gas sensor unit 210 is provided with sensor chamber 212 bored cylindrically from the top of gas sensor unit 210 almost at the central part of a casing 211 of metal made block members. On one side of sensor chamber 212, an inlet vent 220 is opened for introducing the exhaust gas due to a fluid communication with the exhaust pipe of engine 1, and on the opposite side, an exhaust vent 222 is opened for exhausting the exhaust gas due to a fluid communication between sensor chamber 212 and the atmosphere. Further, within substantially cylindrical sensor chamber 212, gas sensor 213 having a smaller diameter and shorter length than sensor chamber 212 and a substantially cylindrical shape is supported, such that its external surface is separated a predetermined distance away from the inner wall of sensor chamber 212.

Gas sensor 213 is substantially the same as gas sensor 13 of the previous embodiment. Gas sensor 213 may be a contact burning-type system wherein the density of a combustible gas, such as CO and the like, is detected by sensing portion 130 comprising a platinum coil as a sensing element. Sensing portion 130 is placed towards the bottom wall of sensor chamber 212, and electrical wires 138 extending from the base side form connecting terminals 134 on the outside surface of a lid member 25 for sealing the opening formed in sensor chamber 212. As depicted in FIG. 3B, wires 136 are connected electrically to the connecting terminals.

Gas sensor 213 is supported substantially at the central part of sensor chamber 212, such that one side of sensing portion 130 is supported from the bottom wall of sensor chamber 212 by elastic supporting member 230 comprised of a vibration damping spring, and the other side is suspended or hung from the inner side of lid 25 of sensor chamber 212 by elastic supporting members 232 comprised of two vibration damping springs. Each elastic supporting member 230 comprises a vibration damping spring and has a diameter of about four times larger than elastic supporting member 232 comprising of a vibration damping spring. Elastic supporting member 232 is disposed so as to support gas sensor 213 from the bottom, and elastic supporting member 232 comprises a vibration damping spring disposed so that wires 138 extending from gas sensor 213 penetrate through the inner side thereof.

Gas sensor unit 210 of the present embodiment has a configuration as described above, and, thus, gas sensor 213 is supported by elastic supporting members 230 and 232 comprised of three vibration damping springs, so that it is freely movable in all directions including not only a vertical direction, but also lateral directions and other directions compounding these together. Moreover, gas sensor 213, unlike a configuration in which gas sensor 213 is supported or suspended by elastic members comprising vibration damping springs from only one direction, does not freely move so excessively as to cause gas sensor 213 to collide with the inner wall of sensor chamber 212 and delayed convergence of its oscillations does not occur. This configuration may effectively prevent the damage to or degradation of the sensing element which is sensitive to vibration.

The elastic supporting parts for supporting gas sensor 213 are not necessarily limited to the elastic supporting parts 230 and 232 comprising of the vibration damping springs, and these parts may be substituted with various means or members, such that the opposing sides of gas sensor 213 pulled by a plurality of opposing rubber belts and the like. Nevertheless, elastic members comprised of springs may be most suitable from the viewpoint of ease of assembling, secure suppression or damping of the vibration, and durability. Further, the location and the number of the elastic members, e.g., the vibration damping springs, are not limited to the present embodiment, and various modifications may be applied, for example, such that gas sensor 213 is supported laterally from opposing sides of sensor chamber 212 or the like.

Moreover, gas sensor unit 210 is directly attached to the carburetor of engine 1, and the carburetor side also is configured accordingly. Therefore, gas sensor unit 210 is configured in the present embodiment in such a way that an exhaust gas returning vent 224 is provided for directly introducing at least a portion of the exhaust gas to the inside of the carburetor, and the volume of the return gas may be controlled appropriately. This configuration improves the state of the exhaust gas, such that the exhaust gas may more readily satisfy the exhaust gas regulations or standards and further provides for reduced manufacturing cost because no extra piping is required to return the exhaust gas.

Although embodiments of the present invention have been described in detail herein, the scope of the invention is not limited thereto. It will be appreciated by those skilled in the art that various modifications may be made without departing from the scope of the invention. Accordingly, the embodiments disclosed herein are only exemplary. It is to be understood that the scope of the invention is not to be limited thereby, but is to be determined by the claims which follow.

What is claimed is:

1. A gas sensor unit for an engine comprising:
   a sensor chamber of said unit;
   a gas sensor adapted to detect a combustible gas, said gas sensor being disposed in said sensor chamber to detect a density of a particular ingredient of said combustible gas contained in an exhaust gas exhausted from a cylinder of said engine, and to output a detection signal to a control unit; and
   means for damping vibration, wherein said means for damping vibration is adapted to support at least one of said gas sensor unit or said combustible gas sensor disposed in said gas sensor unit, such that said gas sensor unit or said combustible gas sensor is movable by an amount equal to or less than a predetermined extent of movement of said engine, thereby to reduce vibration from said engine from transmitting directly to said gas sensor unit or said combustible gas sensor.

2. The gas sensor unit of claim 1, wherein means for damping vibration comprises an elastic supporting member for supporting said gas sensor unit separate from said engine, and
   wherein an exhaust gas inlet pipe, which branches and extends from an exhaust pipe of said engine, is connected to said gas sensor unit to conduct said exhaust gas into said sensor chamber.

3. The gas sensor unit of claim 2, wherein said elastic supporting member comprises a ring-shaped, hanging band made of an elastic material, said hanging band hanging said gas sensor unit from said engine.

4. The gas sensor unit of claim 1, wherein said gas sensor unit is fixedly mounted onto said engine and,
   wherein said means for damping vibration comprises an elastic supporting member, which supports said gas sensor separate from an inner wall of said sensor chamber.

5. The gas sensor unit of claim 4, wherein said elastic supporting member comprises a vibration-damping spring.

6. The gas sensor unit of claim 5, wherein said vibration damping spring is adapted to support at least a top side and a base side of said gas sensor in two directions from said inner wall of said sensor chamber.

7. The gas sensor unit of claim 4, wherein said gas sensor unit is fixedly attached to and integral with a carburetor of said engine and
   wherein an exhaust gas return passageway adapted to return to said carburetor, at least a portion of said exhaust gas introduced into said sensor chamber.

8. The gas sensor unit of claim 5, wherein said gas sensor unit is fixedly attached to and integral with a carburetor of said engine and
   wherein an exhaust gas return passageway adapted to return to said carburetor, at least a portion of said exhaust gas introduced into said sensor chamber.

9. The gas sensor unit of claim 6, wherein said gas sensor unit is fixedly attached to and integral with a carburetor of said engine and
   wherein an exhaust gas return passageway adapted to return to said carburetor, at least a portion of said exhaust gas introduced into said sensor chamber.

10. The gas sensor unit of claim 1, wherein said gas sensor comprises a combustible gas sensor comprising a platinum coil as a sensing element.

11. The gas sensor unit of claim 2, wherein said gas sensor comprises a combustible gas sensor comprising a platinum coil as a sensing element.

12. The gas sensor unit of claim 3, wherein said gas sensor comprises a combustible gas sensor comprising a platinum coil as a sensing element.

13. The gas sensor unit of claim 4, wherein said gas sensor comprises a combustible gas sensor comprising a platinum coil as a sensing element.

14. The gas sensor unit of claim 5, wherein said gas sensor comprises a combustible gas sensor comprising a platinum coil as a sensing element.

15. The gas sensor unit of claim 6, wherein said gas sensor comprises a combustible gas sensor comprising a platinum coil as a sensing element.

16. The gas sensor unit of claim 7, wherein said gas sensor comprises a combustible gas sensor comprising a platinum coil as a sensing element.

17. The gas sensor unit of claim 8, wherein said gas sensor comprises a combustible gas sensor comprising a platinum coil as a sensing element.

18. The gas sensor unit of claim 9, wherein said gas sensor comprises a combustible gas sensor comprising a platinum coil as a sensing element.

19. An engine comprising a gas sensor unit for an engine, said gas sensor unit comprising:
    a sensor chamber of said unit;
    a gas sensor adapted to detect a combustible gas, said gas sensor being disposed in said sensor chamber to detect a density of a particular ingredient of said combustible gas contained in an exhaust gas exhausted from a cylinder of said engine, and to output a detection signal to a control unit; and
    means for damping vibration, wherein said means for damping vibration is adapted to support at least one of said gas sensor unit or said combustible gas sensor disposed in said gas sensor unit, such that said gas sensor unit or said combustible gas sensor is movable by an amount equal to or less than a predetermined extent of movement of said engine, thereby to reduce vibration from said engine from transmitting directly to said gas sensor unit or said combustible gas sensor.

20. The engine of claim 19, wherein said gas sensor unit is fixedly attached to and integral with a carburetor of said engine and wherein an exhaust gas return passageway adapted to return to said carburetor, at least a portion of said exhaust gas introduced into said sensor chamber.

* * * * *